United States Patent [19]

Lyons, Jr.

[11] Patent Number: 5,054,906
[45] Date of Patent: Oct. 8, 1991

[54] INDIRECTLY ILLUMINATING OPHTHALMOLOGICAL SPECULUM

[75] Inventor: William G. Lyons, Jr., West Brookfield, Mass.

[73] Assignee: Brimfield Precision, Inc., Brimfield, Mass.

[21] Appl. No.: 819,675

[22] Filed: Jan. 17, 1986

[51] Int. Cl.⁵ ............................................. A61B 3/10
[52] U.S. Cl. ....................................... 351/205; 128/18
[58] Field of Search .................. 351/205; 128/3, 4, 6, 128/11, 20, 18

[56] References Cited

U.S. PATENT DOCUMENTS

| | | |
|---|---|---|
| 2,702,540 | 2/1955 | Debeh . |
| 3,626,471 | 12/1971 | Florin ................................. 128/20 |
| 3,680,546 | 8/1972 | Asrican ............................... 128/18 |
| 4,265,519 | 5/1981 | Pomerantzetf ...................... 351/205 |
| 4,337,763 | 7/1982 | Petrassevich ........................ 128/20 |
| 4,556,052 | 12/1985 | Muller ................................. 128/11 |

Primary Examiner—Paul M. Dzierzynski

[57] ABSTRACT

An ophthalmological apparatus for opening the eyelids to permit access to the eye, and for illuminating the eye, primarily suited for ophthalmological procedures upon the surface of the eye. In one embodiment, a pair of optical fibers is provided along the arms of a speculum.

8 Claims, 1 Drawing Sheet

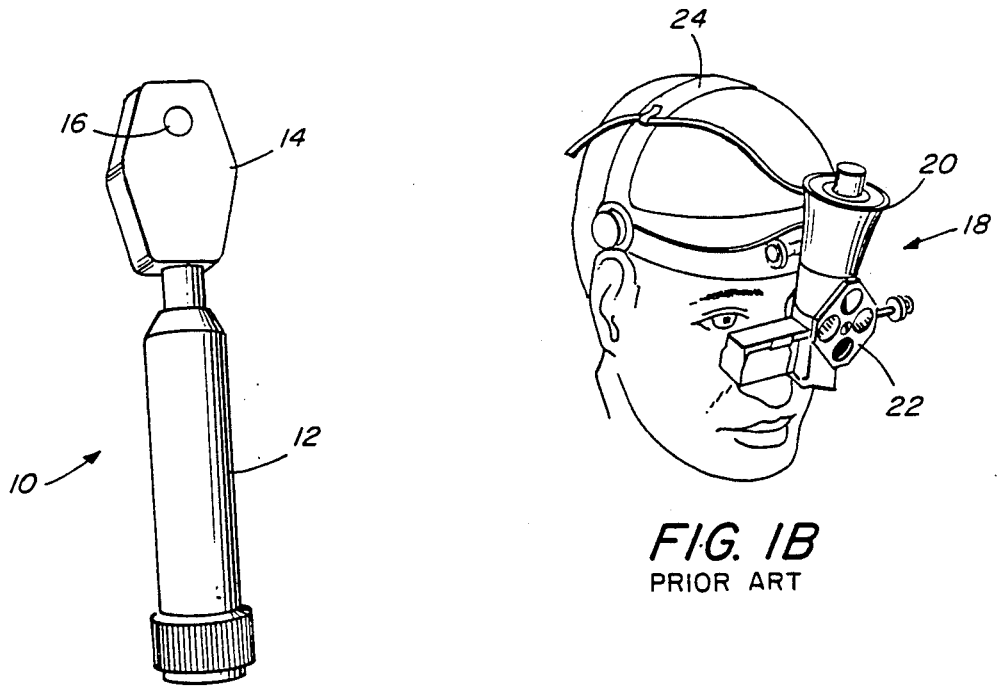
FIG. IA
PRIOR ART
FIG. IB
PRIOR ART
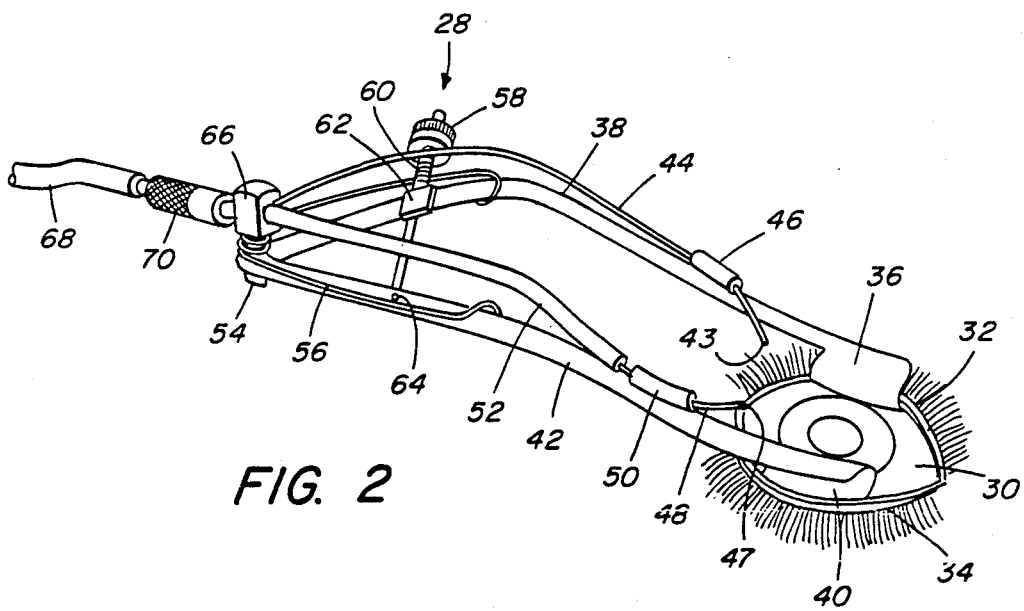
FIG. 2

5,054,906

INDIRECTLY ILLUMINATING OPHTHALMOLOGICAL SPECULUM

BACKGROUND OF THE INVENTION

This invention relates to an ophthalmological apparatus and more particularly to an indirectly illuminating ophthalmological speculum primarily for use in diagnosis and treatments of the surface of the eye.

Ophthalmology is that branch of medicine which involves the eye, its diseases and defects, and its treatment. Many ophthalmological procedures are concerned with the surface of the eye, such as work on the lens, and treatment for cataracts and corneal diseases. Typically, an instrument called an ophthalmoscope is used to assist the ophthalmologist in these procedures.

Although Hermann von Helmholtz, a German physicist and physiologist, is generally credited with inventing the first ophthalmoscope in the early 1850's, there is some evidence that the English mathematician Charles Babbage, was actually the first inventor, some five or ten years earlier. In any event, the modern ophthalmoscope has changed very little from the one envisioned by Babbage or Helmholtz well over 100 years ago. The typical ophthalmoscope includes a tube, a light source such as a light bulb, a mirror at one end of the tube which shines the light through the tube and out the end pointed toward the patient, and a lens which magnifies the view that the ophthalmologist has of the patient's eye. The primary value of the ophthalmoscope is that it permits the ophthalmologist a clear view of the interior and the back surface of the eye. Owing to the lack of a more useful instrument, ophthalmoscopes are typically used for work on the surface of the eye, as well as the interior. While they do provide magnification for the ophthalmologist, and a light source that illuminates the exterior as well as the interior of the eye, these instruments present a number of problems when being used for procedures upon the surface of the eye.

First of all, an ophthalmoscope which is to be used in conjunction with treatment rather than mere examination of the eye, is one which must leave the ophthalmologist's hands free. Such an ophthalmoscope would generally be of the type that is mounted upon the physician's head, rather than the handheld type. In order to provide sufficient illumination from this remote location, the light beam must be narrowly focused and intense. For many procedures the patient remains conscious and finds this intense, narrowly focused light beam extremely uncomfortable. Additionally, there are some indications that the strong narrow light beam may cause damage to the rear of the eye.

Ophthalmoscopes which are worn on the heads of ophthalmologists are also unduly heavy, cumbersome, and uncomfortable to the doctor, because of their self-contained light and power sources.

It can thus be seen that while the traditional ophthalmoscope is useful for procedures involving the interior of the eye, it is ill suited for work upon the surface of the eye.

In addition to the ophthalmoscope a speculum device is often employed to separate the eyelids to provide the ophthalmologist with an unobstructed field to perform procedures such as cataract removal or lens transplants. A typical speculum includes a pair of arms with hooked ends for engaging the eyelids, and a spring for keeping the arms separated.

It is, therefore, an object of this invention to provide a medical instrument for ophthalmological procedures, ideally suited for work on the surface of the eye, which provides illumination that is comfortable for the patient while at the same time maintaining the eyelids separated. It is a further object of this invention to provide an ophthalmological instrument which is safe and avoids the type of damage to the retina, cones, rods, and other parts of the eye that might be caused by intensely focused light. Yet another object of this invention is to provide for the comfort of the ophthalmologist by allowing him or her to wear a lightweight magnifying instrument which need not include a heavy light source. Still another object of this invention is to provide for even, diffuse, substantially tangential illumination of the eye without shadows. A further object of this invention is to provide illumination of the eye without obstruction. These and other objects will in part be apparent and in part pointed out hereinafter.

SUMMARY OF THE INVENTION

The indirectly illuminating ophthalmological speculum disclosed herein for use in diagnosis and treatment of the surface of the eye includes a speculum which has a hookend on each of its arms, which opens a pair of eyelids. In a preferred embodiment, two optical fibers are aimed to project light substantially tangential to the surface of the eye, by rigid tubes which are attached to the arms of the speculum by connecting tubes. Along one arm the optical fiber is fixed within the rigid tube which runs the length of the arm. Along the second arm, the short rigid tube feeds in to a flexible tube which allows the optical fiber to bend as the arms of the speculum are moved in and out. These arms rotate about a small screw joining the two arms, and the arms are held apart by a helical spring which has legs pushing outward on the two arms. The amount that the two arms open is regulated by the position of a knurled nut on the end of a threaded rod which passes through a bracket attached to the first arm. The threaded rod is pivotally attached to the second arm by a rivet. Located near the axis of rotation of the two arms, is an optical fiber junction to which the two optical fibers attach. This optical fiber junction is connected to a long flexible light feed tube by a detachable connector. In operation, the remote end of the flexible light feed tube would be connected to some external light source.

BRIEF DESCRIPTION OF THE DRAWING

The invention disclosed herein will be better understood with reference to the following drawing of which:

FIGS. 1A and 1B are perspective views of examples of the prior art; and

FIG. 2 is a perspective view showing one embodiment of this invention being used in an ophthalmological procedure.

DETAILED DESCRIPTION OF THE PREFERRED EMBODIMENT

With reference first to FIGS. 1A and 1B, two ophthalmoscopes which are typical examples of the prior art are shown. A handheld ophthalmoscope 10 includes a strong light source 12 which casts light into an eyepiece 14. Within the eyepiece, the light is reflected out of a lens 16 onto an eye being examined. An ophthalmologist views the eye through the lens 16. Of course, this handheld device is suitable only for examination, and not for treatment. Alternatively, a headgear ophthalmoscope 18 includes a light source 20, a lens 22 for viewing an eye, and a headpiece 24 for carrying the ophthalmoscope upon an ophthalmologist's head. Although the ophthalmoscope 18 is a monocular model, binocular versions are also known in the art.

FIG. 2 shows the present invention 28 being used in an ophthalmological procedure on an eye 30 wherein a first eyelid 32 and a second eyelid 34 are held open to permit access to the eye 30 by a first hookend 36 on a first arm 38 and a second hookend 40 on a second arm 42. An optical fiber 43 which is useful in illuminating the eye is carried within a first rigid tube 44 which is attached to the first arm 38 by a first connecting tube 46. A second optical fiber 47 is carried within a second rigid tube 48, which is shorter than the first rigid tube 44, and which is attached to the second arm 42 by a second connecting tube 50. The two rigid tubes 44 and 48 are positioned to direct light from the two optical fibers 43 and 47 substantially tangential to the eye 30 to avoid painful and potentially harmful light being focused directly into the eye 30 as in the prior art.

The second rigid tube 48 leads into a flexible tube 52 permitting the second arm 42 to rotate through a screw 54 about the first arm 38. A helical spring 56 imparts a force to the first arm 38 and the second arm 42 causing them to move apart. The angle that the arms move apart is regulated by the position of a knurled nut 58 upon a threaded rod 60 which passes through a bracket 62 mounted to the first arm 38 and which is pivotally connected to the second arm 42 by a rivet 64. The first rigid tube 44 and the flexible tube 52 both connect to an optical fiber junction 66. A flexible light feed tube 68 carries another optical fiber from a remote light source (not shown), and connects to the junction 66 through a detachable connector 70.

In preparation for an ophthalmological procedure upon the surface of the eye 30, the ophthalmologist would take the illuminating speculum 20 disclosed herein decoupled from the external light source and insert the hookends 36 and 40 under the eyelids 32 and 34 and slowly rotate the knurled nut 58 permiting helical spring 56 to push the arms 38 and 42 apart thus presenting the surface of the eye accessible for the procedure. The ophthalmologist would then take the flexible light feedtube 68 and connect it to the fiber junction 66 with the detachable connector 70. Once the external light source was enabled, the surface of the eye would be amply illuminated by gentle and diffuse substantially tangential light, so that the ophthalmologist could easily go forward with the procedure, unobstructed by the structure of the light source and with less discomfort to both the patient and the doctor. If the ophthalmologist desired magnification, he or she could wear a light-weight monocular or binocular eyepiece.

It is thus seen that the objects of this invention have been achieved in that there has been disclosed an indirectly illuminating ophthalmological speculum which amply illuminates the surface of the eye and separates the eyelids, which is comfortable to the patient, which avoids the type of damage that may be occasioned by intense light directed into the eye, which fully illuminates the entire surface of the eye, which provides for the comfort of the ophthalmologist, which does not obstruct the work area, which is inexpensive, which is easy to use, and which is far better suited for work on the surface of the eye than the ophthalmoscopes of the prior art.

While this invention is primarily intended to assist in ophthalmological procedures upon the surface of an eye, and it is believed that the invention would have its greatest utility in such application, it is to be understood that this use is not intended as any limitation. This invention would also be useful assisting internal surgical procedures upon the eye, for example, even with concurrent use of a traditional ophthalmoscope.

It is recognized that variations and modifications such as the use of Light Emitting Diodes, semiconductor lasers, or small light bulbs, to provide illumination in place of the optical fibers disclosed in conjunction with the preferred embodiment of FIG. 2, will be apparent to those skilled in the art and it is intended that all such variations and modifications be included within the scope of the appended claims.

What is claimed is:

1. Ophthalmological apparatus comprising:
   means for urging a pair of eyelids open without obstructing access to the eye so that a surgical procedure may be performed thereon; and
   eye illuminating means mounted to said eyelid opening means positioned to direct light substantially tangential to the surface of an eye.

2. The apparatus of claim 1 wherein said eye illuminating means includes an optical fiber.

3. The apparatus of claim 1 wherein said eye illuminating means includes a plurality of optical fibers.

4. The apparatus of claim 3 wherein said eyelid opening means includes
   a first arm;
   a second arm pivotally connected to said first arm;
   means for urging said first and second arms apart, mounted to the arms; and
   means for regulating the separation of said first arm from said second arm.

5. The apparatus of claim 1 wherein said eyelid opening means includes
   a first arm;
   a second arm pivotally connected to said first arm;
   means for urging said first and second arms apart, mounted to the arms; and
   means for restricting the separation of said first arm from said second arm.

6. The apparatus of claim 4 wherein a first optical fiber is rigidly affixed to said first arm; and
   a second optical fiber is flexibly affixed to said second arm, so that said second optical fiber permits pivotal motion of said second arm about said first arm.

7. The apparatus of claim 6 wherein said eye illuminating means includes means for detachably connecting to a light source.

8. The apparatus of claim 1 wherein said eye illuminating means includes means for detachably connecting to a light source.

* * * * *